United States Patent
Song et al.

(10) Patent No.: US 9,926,361 B2
(45) Date of Patent: *Mar. 27, 2018

(54) PROCESS FOR PRODUCING AND PURIFYING FACTOR VIII AND ITS DERIVATIVES

(71) Applicant: SK CHEMICALS CO., LTD., Gyeonggi-Do (KR)

(72) Inventors: In-Young Song, Seoul (KR); Hun-Taek Kim, Seoul (KR); Jong-Wan Kim, Seoul (KR); Yong-Kook Kim, Gyeonggi-do (KR); Jong-Il Ryu, Gyeonggi-do (KR); Dae-Kee Kim, Seoul (KR)

(73) Assignee: SK CHEMICALS CO., LTD., Gyeonggi-Do (KR)

( * ) Notice: Subject to any disclaimer, the term of this patent is extended or adjusted under 35 U.S.C. 154(b) by 0 days.

This patent is subject to a terminal disclaimer.

(21) Appl. No.: 15/236,092

(22) Filed: Aug. 12, 2016

(65) Prior Publication Data

US 2016/0347819 A1    Dec. 1, 2016

Related U.S. Application Data

(63) Continuation of application No. 12/528,204, filed as application No. PCT/KR2007/000947 on Feb. 23, 2007, now Pat. No. 9,441,030.

(51) Int. Cl.
C07K 14/755 (2006.01)
C07K 1/22 (2006.01)

(52) U.S. Cl.
CPC .............. *C07K 14/755* (2013.01); *C07K 1/22* (2013.01)

(58) Field of Classification Search
None
See application file for complete search history.

(56) References Cited

U.S. PATENT DOCUMENTS

| | | | |
|---|---|---|---|
| 4,522,751 A | 6/1985 | Linnau et al. | |
| 5,112,950 A | 5/1992 | Meulien et al. | |
| 5,422,250 A | 6/1995 | Mignot et al. | |
| 5,661,008 A | 8/1997 | Almstedt et al. | |
| 5,707,832 A | 1/1998 | Mignot et al. | |
| 5,851,800 A | 12/1998 | Adamson et al. | |
| 6,171,825 B1 | 1/2001 | Chan et al. | |
| 6,300,100 B1 | 10/2001 | Kamei et al. | |
| 7,041,635 B2 | 5/2006 | Kim et al. | |
| 2002/0025556 A1 | 2/2002 | Fischer et al. | |

FOREIGN PATENT DOCUMENTS

| | | |
|---|---|---|
| CN | 1745100 A | 3/2006 |
| EP | 0 127 603 A | 12/1984 |
| EP | 0 306 963 A | 3/1989 |
| EP | 07709081.9 | 12/2009 |
| JP | A-H06-113879 | 4/1994 |
| KR | 10-2009-7017650 | 8/2009 |
| WO | WO 90/02175 A | 3/1990 |
| WO | WO 91/09122 A | 6/1991 |
| WO | WO 99/46299 | 9/1999 |
| WO | WO 2008/102923 A1 | 8/2008 |

OTHER PUBLICATIONS

The Journal of Biological Chemistry, vol. 263, No. 13, pp. 6352-6362 (1988), publication date: May 5, 1988.
The Journal of Clinical Investigation, vol. 82, pp. 1236-1243 (1988), publication date: Oct. 30, 1988.
Blood., vol. 85, pp. 3150-3157, publication date: Jun. 1, 1995.
FEBS Letters, vol. 306, pp. 243-246 (1992), publication date: Jul. 31, 1992.
Biochem. J., vol. 277, pp. 23-31 (1991), publication date: Dec. 31, 1991.
Hematology 2005, pp. 429-435 (2005), publication date: Dec. 31, 2005.
Scientific Discussion (2004) on KOGENATE Bayer (recombinant FVIII product) by The European Agency for the Evaluation of Medicinal Products (EMEA), publication date: Dec. 31, 2004, publication date: Dec. 31, 2001.
Current Opinion in Biotechnology, 12:180-187 (2001).
English Translation of the Invalidation Action against corresponding Chinese Patent No. ZL200780051622.5 filed on Jun. 30, 2016.
Vlot, AJ et al.: "The affinity and stoichiometry of binding of human factor VIII to von Willebrand factor", *blood*, Jun. 1, 1995, vol. 85, No. 11, pp. 3150-3157.
Kaijio, Tomoko et al.: "Stabilization of basic fibroblast growth factor with dextran sulfate", *FEBS Letters*, vol. 306, No. 2, 3, pp. 243-246, Jul. 1992.
Koedam, Johannes A. et al.: "Inactivation of Human Factor VIII by Activated Protein C, Cofactor Activity of Protein S and Protective Effect of von Willebrand Factor", *J. Clin. Invest.*, vol. 82, Oct. 1988, pp. 1236-1243.
Chen, Jyh-Ping: "Novel Affinity-Based Processes for Protein Purification", *Journal of Fermentation and Bioengineering*, vol. 70, No. 3, pp. 199-209, 1990.
Scientific Discussion for the approval of Kogenate Bayer,*EMEA*, 2004, pp. 1/13-13/13.
Plaintiff's First Submission from an Invalidation Trial initiated by a third party against corresponding Korean Patent No. 10-1389376 (application No. 10-2009-7017650) dated Jul. 28, 2014, English translation.

(Continued)

*Primary Examiner* — Suzanne M Noakes
*Assistant Examiner* — Jae W Lee
(74) *Attorney, Agent, or Firm* — Haug Partners LLP (57) ABSTRACT

Disclosed is a method for producing proteins having factor VIII procoagulant activity in serum-free medium by in vitro culturing of mammalian cells, wherein the serum-free medium contains an inhibitor against the protease released from cultured cells. In accordance with this invention, the inhibitor can protect the cleavage of a target protein during cultivation and increase homogeneity of a target molecule, wherein the inhibitor can be a dextran sulfate. This invention also relates to a method of purifying target molecules from the culture medium containing both a target molecule and selected inhibitors by affinity chromatography.

5 Claims, 5 Drawing Sheets

(56) References Cited

OTHER PUBLICATIONS

Plaintiff's Second Submission (in response to Defendant's Assertion) from an Invalidation Trial initiated by a third party again corresponding Korean Patent No. 10-1389376 (application No. 10-2009-7017650), English translation.
Defendant's First Submission from an Invalidation Trial initiated by a third party against corresponding Korean Patent No. 10-1389376 (application No. 10-2009-7017650) dated Oct. 1, 2014, with full English translation.
Defendant's Second Submission from an Invalidation Trial initiated by a third party against corresponding Korean Patent No. 10-1389376 (application No. 10-2009-7017650) dated May 28, 2015 with full English translation.
Plaintiff's Second Submission (in response to Defendant's Assertion) from an Invalidation Trial initiated by a third party against corresponding Korean Patent No. 10-1389376 (application No. 10-2009-7017650), dated Nov. 5, 2014, English translation.
Innova Bioscience ATP Agarose High (Product Insert, first available online on Jul. 31, 2004, see the attached Google publication date indicated with an arrow).
Recombinate Prescribing Information, U.S. License No. 140, Baxter Healthcare Corporation, Westlake Village, CA 91362 USA.
Advate Prescribing Information, USBS/34/14-0101, Issued Apr. 2014, U.S. License No. 140, Baxter Healthcare Corporation, USA.
Kogenate Prescribing Information, U.S. License No. 8,(License Holder: Bayer Corporation) Bayer HealthCare LLC, Whippany, NJ, USA.
Fay et al. (The Journal of Biological Chemistry vol. 274, No. 42, Issue of Oct. 15, pp. 29826-29830, 1999).
Kessler (New perspectives in hemophilia treatment. Hematology Am Soc Hematol Educ Program. 2005:429-35).
Cutler (Protein Purification Protocols, Second Edition, vol. 244, Methods in Molecular Biology, 2004, Humana Press Inc., pp. 173 and 187).
Database WPI Week 200682—Thomson Scientific—XP002685399.
Debra D. Pittman and Randal J. Kaufman, "Structure-Function Relationships of Factor VIII Elucidated Through Recombinant DNA Technology", *F.K. Schattauer Verlagsgesellschaft mbH*, 1989, 161-165, 61(2).
Chen et al. (Journal of Fermentation and Bioengineering, vol. 70, No. 3, 199-209, 1990).
Sandberg, H. et al.: "Mapping and Partial Characterization of Proteases Expressed by a CHO Production Cell Line", *Biotechnology and Bioengineering*, vol. 95, No. 5, Dec. 5, 2006, pp. 961-971.

Satoh, Mitsuo et al.: "Chinese Hamster Ovary Cells Continuously Secrete a Cysteine Endopeptidase", *Vitro Cell. Dev. Biol*, 26, Nov. 1990, pp. 1101-1104.
Chen, Zhaolie et al.: "A low-cost chemically defined protein free medium for a recombinant CHO cell line producing prothrombin", *Biotechnology Letters*, 22, 2000, pp. 837-841.
Jenkins, Nigel et al.: "Getting the glycosylation right: Implications for the biotechnology industry", *Nature Biotechnology*, vol. 14, Aug. 1996, pp. 975-961.
Brooks, Susan A. et al.: "Appropriate Glycosylation of Recombinant Proteins for Human Use, Implications of Choice of Expression System", *Molecular Biotechnology*, vol. 28, 2004, pp. 241-255.
Mols, J. et al.: "Recombinant Interferon-γ Secreted by Chinese Hamster Ovary-320 Cells Cultivated in Suspension in Protein-Free Media is Protected Against Extracellular Proteolysis by the Expression of Natural Protease Inhibitois and by the Addition of Plant Protein Hydrolysates to the Culture Medium", In Vitro *Cell Div Biol—Animal*, 41, Mar. and Apr. 2005, pp. 83-91.
Fay, Philip J. et al.: "The size of human factor VIII heterodimers and the effects produced by thrombin", *Biochimica et Biophysica Acta*, 871 (1986), pp. 268-278.
Toole, John J. et al.: "A large region (=95 kDa) of human factor VIII is dispensable for in vitro procoagulant activity", *Proc Natl. Acad. Sci USA*, vol. 83, Aug. 1986, pp. 5939-5942.
Burke, Rae Lyn et al.: "The Functional Domains of Coagulation Factor VIII:C", *The Journal of Biological Chemistry*, vol. 261, No. 27, Issue of Sep. 25, 1986, pp. 12574-12578.
Eaton, Dan L. et al.: "Construction and Characterization of an Active Factor VIII Variant Lacking the Central One-Third of the Molecule",*Biochemistry*, vol. 25, No. 26, Dec. 30, 1986, pp. 8343-8347.
Chu, Lily et al.: "Industrial choices for protein production by large-scale cell culture", *Current Opinion in Biotechnology*, 2001, 12, pp. 180-187.
Chotteau, Veronique et al.: "Development of a Large Scale Process for the Production of Recombinant Truncated Factor VIII in CHO Cells under Cell Growth Arrest Conditions", *E. Lindner-Olsson et al. eds. J.Animal Cell Technology: From Target to Market*, 2001, pp. 287-291.
Vehar, Gordon A. et al.: "Structure of human factor VIII", *Nature*, 312, 1984, pp. 337-342.
Toole, John J. et al.: "Molecular cloning of a cDNA encoding human antihaemophilic factor", *Nature*, 312, 1984, pp. 342-347.
Eaton, Dan et al.: "Proteolytic Processing of Human Factor VIII. Correlation of Specific Cleavages by Thrombin, Factor Xa, and Activated Protein C with Activation and Inactivation of Factor VIII Coagulant Activity",*Biochemistry*, 1986, 25, pp. 505-512.
Lynch, Carmel M. et al.: "Sequences in the Coding Region of Clotting Factor VIII Act as Dominant Inhibitors of RNA Accumulation and Protein Production", *Human Gene Therapy*, 4, 1993, pp. 259-272.

PROCESS FOR PRODUCING AND PURIFYING FACTOR VIII AND ITS DERIVATIVES

This Application is a Continuation of patent application Ser. No. 12/528,204, filed Aug. 21, 2009, which is a National Stage entry under 35 U.S.C. § 371 of International Application No. PCT/KR2007/000947 filed on Feb. 23, 2007, published on Aug. 28, 2008 under publication number WO 2008/102923 A1, the entirety of which is incorporated herein by reference.

BACKGROUND ART

Factor VIII is a plasma glycoprotein involved in blood coagulation. Deficiency or abnormality in its function results in severe hereditary disease called hemophilia A (Eaton, D. et al., 1986, Biochemistry 25: 505-512; Toole, J. J. et al., 1984, Nature 312: 342-347; Vehar, G. A. et al., 1984, Nature 312: 337-342). Up to now, the only treatment for hemophilia A has been intravenous administration of factor VIII prepared from human blood or a recombinant source. Due to the safety reason, recombinant factor VIII has been preferred to plasma derived factor VIII. However, since expression level of factor VIII is 2-3 order magnitudes lower than other molecules in the same expression system (Lynch C. M., 1993, Human Gene Therapy 4: 259-272), recombinant factor VIII production has not met its demand.

Several attempts have achieved an improved expression of factor VIII by removing B-domain which has been known not to have any function in the cofactor activity of factor VIII (Eaton et al., 1986, Biochemistry 25:8343-8347; Burke, R. L. et al., 1986, J. Biol. Chem., 261: 12574-12578; Toole, J. J. et al., 1986, Proc. Natl. Acad. Sci. USA, 83: 5939-5942; Fay et al., 1986, Biochem. Biophys. Acta, 871:268-278). U.S. Pat. No. 5,661,008 and WO-A-91/09122 described B-domain deleted versions of factor VIII, which is similar to the shortest form of plasma factor VIII. U.S. Pat. Nos. 5,112,950 and 7,041,635 disclosed the single chain forms of B-domain deleted factor VIII molecules.

As a choice for the mammalian cell expression, Chinese Hamster Ovary (CHO) cell expression system has been used in producing many therapeutic proteins including factor VIII (Chu, L et al., 2001, Curr. Opin. Biotehnol., 12: 180-187). The characteristics of CHO cell line are elucidated. It can grow either in anchorage dependent manner or in suspension manner, adapt to either serum-containing medium or serum-free medium, and especially support post-translational modifications of proteins nearly identical to the human glycosylation patterns (Brooks S. A., 2004, Mol. Biotechnol., 28: 241-255; Jenkins, N., et al., 1996, Nat. Biotechnol., 14: 975-981; Chen, Z., et al., 2000, Biotechnol. Lett., 22: 837-941; Mols, J., et al., 2005, 41: 83-91). CHO cell lines producing therapeutic proteins have been usually cultured in the animal-derived protein free medium for the purpose of addressing safety concerns about transmission of animal derived virus or prion and for the purpose of easier purification. (Chu, L., et al., 2001, Curr. Opin. Biotehnol., 12: 180-187). However, removal of serum from the cultivating media also deprives the naturally contained protease inhibitors in a serum supplement and makes it difficult to maintain the viability of the cells during the production processes (Mols, J., et al., 2005, 41: 83-91; Sandberg, H., et al., 2006, Biotechnol Bioeng., 95: 961-971).

Reduced viability and stressful conditions seem to increase the production of secreted or released proteases from dead cells which can attack the therapeutic proteins and cause heterogeneity. Heterogeneity caused by internal cleavages of therapeutic protein might be the major problem because cleaved proteins can be inactive and make it difficult to maintain "lot to lot" consistency during the production and purification processes. Therefore, it is important to maintain a relatively low level of protease or to prevent protease activity during production.

A few successful efforts to prevent this proteolysis caused by released proteases from CHO cell line during culture have been reported, even though universal inhibitor(s) which could apply to all therapeutic proteins produced in CHO cell line has not yet been found. Satoh M et al. reported the presence of cystein and serine proteases released from CHO cell. Chotteau et al. (Chotteau, V., et al., 2001, in Animal cell technology: from target to market, Kluwer Academic publishers, pp. 287-292) found that an unidentified, extracellular metal-dependent protease from CHO cell culture medium was responsible for the proteolysis of truncated factor VIM In WO-A-90/02175, it is disclosed that some serine or cysteine proteases from CHO cell culture can be blocked by the inhibitor peptides, which increase factor VIII productivity. EP A 0 306 968 discloses addition of aprotinin to culture medium increased expression of factor VIII in CHO cell medium by three times.

In U.S. Pat. No. 5,851,800, inventors claimed the inhibitors of metalloproteases and chymotrypsins could reduce detrimental effect on factor VIII production in cell culture. Sandberg H. et al. characterized two types of proteolytic activities released by CHO cells in a cell culture. One was originated from metalloproteinases, and the other from serine protease. Only metalloproteinases was found to have a strongly negative effect on the factor VIII activity. However, even though inhibitor of metalloproteases such as EDTA and 1,10 o-phenantroline could block the factor VIII cleavage as described by Sandberg H. et al., these inhibitors cannot be directly added into the CHO cell culture medium due to its toxic effect on cells, judged from our experiments.

All the above-mentioned protease inhibitors and commercially available protease cocktail which contain inhibitors against serine, cystein, aspartic and aminopeptidases such as aprotinin, bestatin, leupeptin, E-64 and pepstatin A have been applied to our single chain factor VIII derivative (described in U.S. Pat. No. 7,041,635) culture, but we found that none of them were effective in protecting our factor VIII derivative from cleavage by released protease(s) from CHO cell culture during the culture.

U.S. Pat. No. 6,300,100 discloses sulfated polysaccharide such as heparin protected an intact Tissue Factor Pathway Inhibitor (TFPI) from cleavage by proteases present in the culture medium. In addition, U.S. Pat. No. 5,112,950 discloses sulfated dextran to substitute the stabilizing effect of Von Willebrand factor on factor VIII in serum free media. However, to our knowledge, there has been no report on the inhibitory effect of dextran sulfate against proteases in connection with factor VIII molecules.

The present invention aims to demonstrate the protective effect of dextran sulfate on the cleavage of Factor VIII or its derivatives from proteases produced during CHO cell culture.

Advantageous Effects

In one aspect of this invention, there is provided a process for the production of Factor VIII or its derivatives in a mammalian host cell line adapted to serum-free media which is supplemented with dextran sulfate. Addition of dextran sulfate in culture media effectively reduced or blocked factor VIII-cleaving activities of (a) certain protease(s) originated from CHO cell culture media and concurrently increased homogeneity of the produced factor VIII molecules. In another aspect of this invention, there is provided an efficient method for purifying factor VIII molecules from dextran sulfate-containing media using monoclonal antibody-based purification steps.

This invention relates to an effective inhibitor which can protect our single chain factor VIII derivatives described in U.S. Pat. No. 7,041,635 from cleavage by protease(s) released during a mammalian host cell cultivation and to increase the homogeneity of the produced factor VIII derivative. Also this invention relates to a method of purifying the factor VIII without being affected by addition of the protease inhibitor.

The mammalian host cell may be any animal cell which can express recombinant factor VIII, and is preferably an animal cell where a desired transformed cell can be easily separated, for example, a Chinese hamster ovary (CHO) cell, BHK cell, or COS cell, and more preferably a CHO cell.

In the previous patent U.S. Pat. No. 6,300,100, there was a description about the protective effects of sulfated polysaccharides on a target protein against certain proteases, in which a target protein was Tissue Factor Pathway Inhibitor (TFPI). Therefore, we tested whether those sulfated polysaccharides could protect our target molecule-factor VIII. This invention showed that only dextran sulfate possesses a very strong protective effect on factor VIII cleavage when added to culture medium during cultivation process.

Dextran sulfate can be obtained from bacterial fermentation or chemical synthesis. The molecular weights of dextran sulfate can vary from 20 to 5,000 kDa in molecular weight, and is preferably 50 to 2,000 kDa.

Sulfur content of dextran sulfate can also vary depending on its source material. Regardless of the sulfur content of dextran sulfate, it can be employed to this invention only if the dextran sulfate can protect factor VIII from cleavage by protease(s) released from a cell cultivation process. The sulfur content of dextran sulfate is preferably in the range of 5 to 20 wt % of sulfated saccharide, more preferably more than 17 wt %.

Depending on the expression level of factor VIII and its host cell line, the amount of dextran sulfate added to a growing media can be adjusted and not limited to those showed in preferred embodiments of this invention.

In one preferred embodiment of this invention, factor VIII molecule is one of the factor VIII derivatives, named dBN (64-53)(hereafter called I2GdBN), which is disclosed in U.S. Pat. No. 7,041,635. This factor VIII derivative has internal deletion in part of B-domain and N-terminal part of A3 and was designed to have a new N-glycosylation recognition sequence in its fusion site. As the method described in example 6 in U.S. Pat. No. 7,041,635, a CHO cell line stably expressing the I2GdBN was prepared and adapted to commercially available serum-free media. Hereinafter this clone is designated as "#39 clone" and all cells mentioned in examples are referred to this CHO cell line (#39).

This invention also relates to a process for purifying factor VIII or derivatives expressed in mammalian host cell line from culture media supplemented with dextran sulfate using an affinity chromatography. The affinity chromatography includes affinity column which contains affinity molecules coupled to solid support such as agarose or sepharose. The affinity molecules can be anti-factor VIII antibodies which can be monoclonal or polyclonal and can be peptides with high affinity to factor VIII.

BEST MODE

This invention is further illustrated with reference to the following Examples, but can be applied to other factor VIII molecules and other cell lines as it will be understood by the skilled person in the art. Therefore, the following examples should not be construed as limiting the scope of this invention.

Heparin, Low molecular weight of heparins (~3 kDa and 4~6 kDa), Dermatan sulfate, dextran (500 kDa), sodium sulfate, dextran sulfate (500 kDa, 10 kDa, 8 kDa) were purchased from Sigma. Dextrans were derived from *Leuconostoc mesenteroides*, strain B 512. Different molecular weights of dextran sulfate were produced by limited hydrolysis and fractionation. Sulfate groups were added by esterification with sulfuric acid under mild conditions. This dextran sulfate contained approximately 17% of sulfur. (http://www.sigmaaldrich.com/sigma-aldrich/product_information_sheet/d6001pis.pdf)

Plating #39 CHO Cell Line

The above-described #39 clone, which is harboring DNA fragment encoding I2GdBN, was cultured in serum free media (ProCHO5 media purchased from Cambrex). At two passages of subculture after thawing, $4 \times 10^5$ cells were seeded in each well of a 6-well plate.

Western Blot Assay

The culture medium containing expressed factor VIII was subjected to 7.5% SDS-PAGE gel and blotted to PVDF membrane. Blotted membrane was probed with an A2 domain-specific antibody called #26-1 which was generated by the inventors of this invention. Secondary mouse IgG coupled with horse-radish peroxidase was used to visualize the factor VIII-anti factor VIII antibody complex on the blot.

EXAMPLE 1

Figure 1:
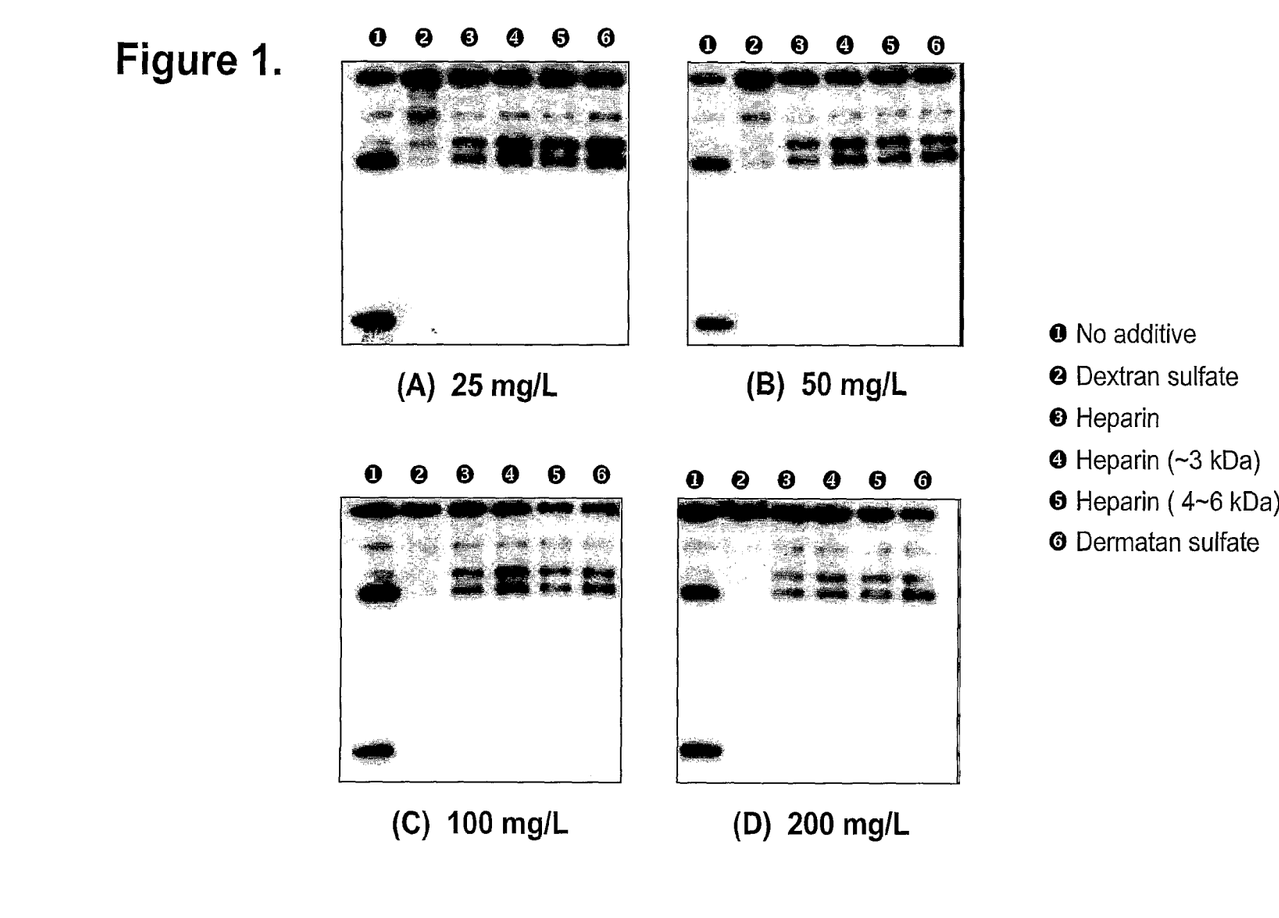
FIG. 1 shows the comparative effects of different sulfated polysaccharides on protecting the cleavage of intact factor VIII.

Comparison of Protective Effect of Various Sulfated Polysaccharides on Fragmentation of 12 GdBN High molecular weight of dextran sulfate (about 500 kDa), heparin, two kinds of low molecular weight heparin (~3 kDa and 4~6 kDa), and dermartan sulfate were purchased from Sigma Co., Ltd. and resuspended in water and filter sterilized. Cells were plated as mentioned above. Twenty-four hours after seeding, the medium was replaced with a fresh one and five kinds of sulfated polysaccharides were added in each well at a final concentration of 25 mg/L, 50 mg/L, 100 mg/L, or 200 mg/L, respectively. After 48 hours incubation, culture supernatants were collected and analyzed through Western blot assay. As shown in FIG. 1, there was little protection effect of three kinds of heparin which were effectively protecting TFPI described in other patents. However, dextran sulfate can provide efficient protection of cleavage and in a concentration-dependent manner. More than 92% of Factor VIII in the culture supernatant (lane 2 in FIG. 1-(D)) remained intact compared to the factor VIIIs in a culture medium with no additives (41%; lane 1 in FIG. 1-(D)) and the factor VIIIs in a culture medium with heparins or dermatan sulfate (52%~67%; lane 3~6 in FIG. 1-(D)). This shows that not all sulfated polysaccharides can protect all the target proteins and the protective effect of a certain sulfated polysaccharide is very specific to a target protein.

EXAMPLE 2

Effect of Molecular Weight of Dextran Sulfate on Cleavage of I2GdBN

Figure 2:
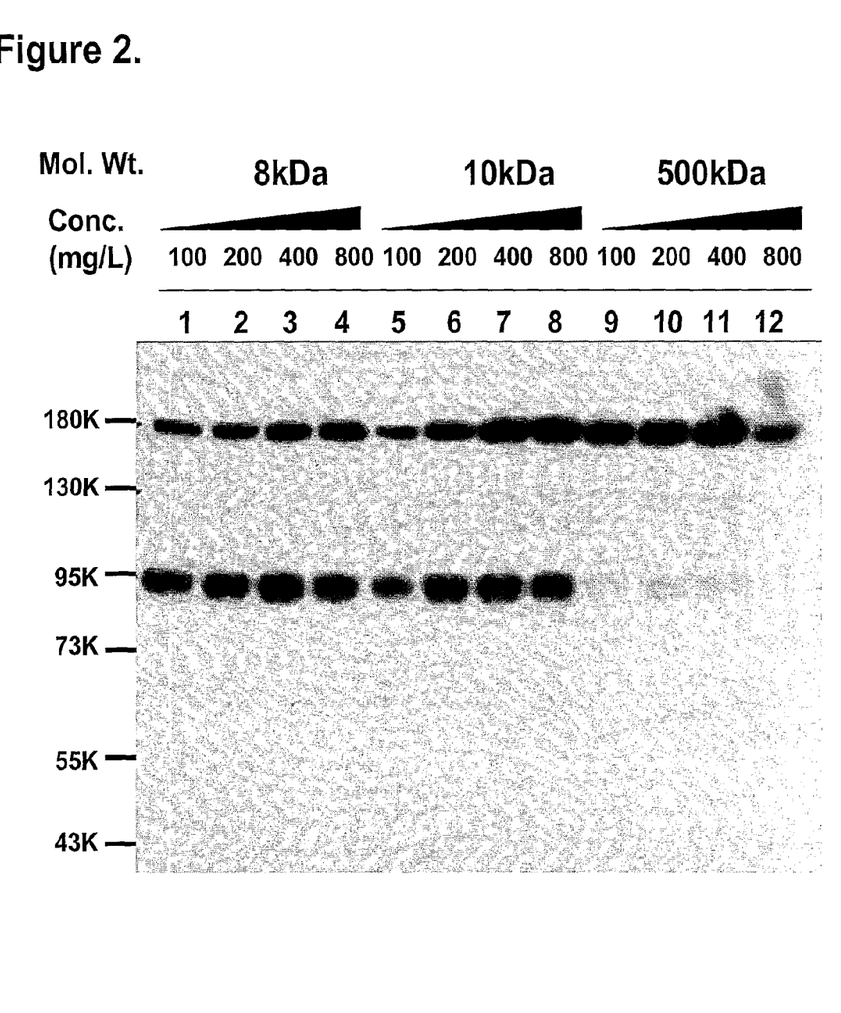
FIG. 2 shows the effects of the molecular weight and concentration of dextran sulfate on the fragmentation of a B-domain deleted factor VIII, I2GdBN.
Figure 3:
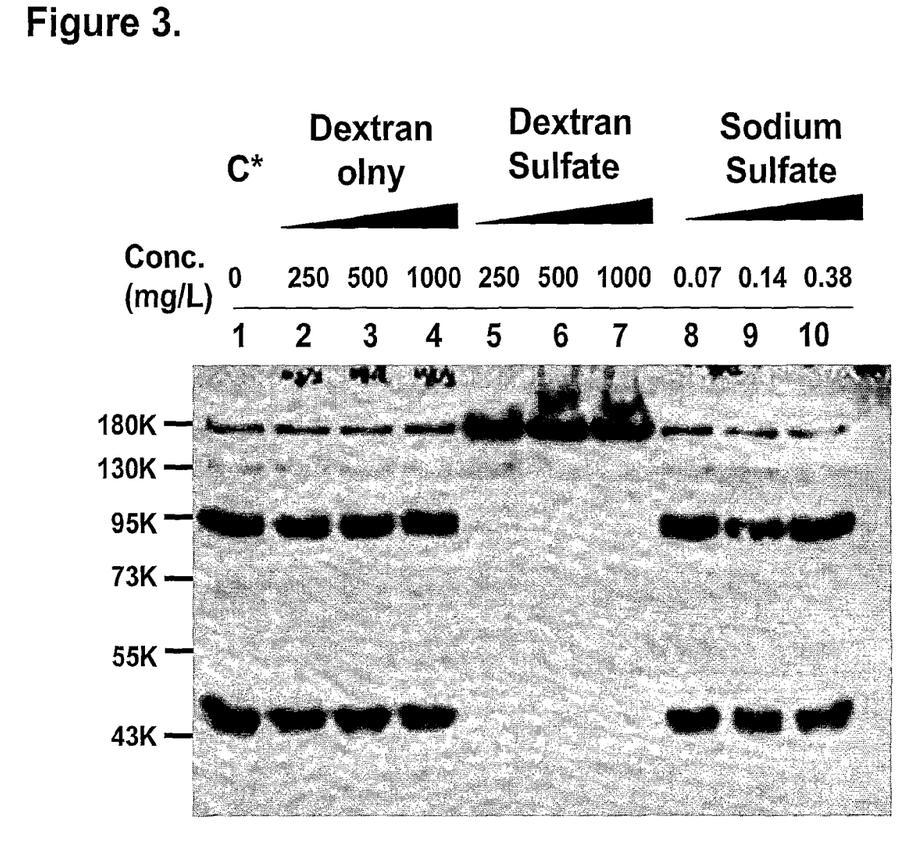
FIG. 3 shows the effects of sulfate, dextran, and dextran sulfate on the fragmentation of I2GdBN.
Figure 4:
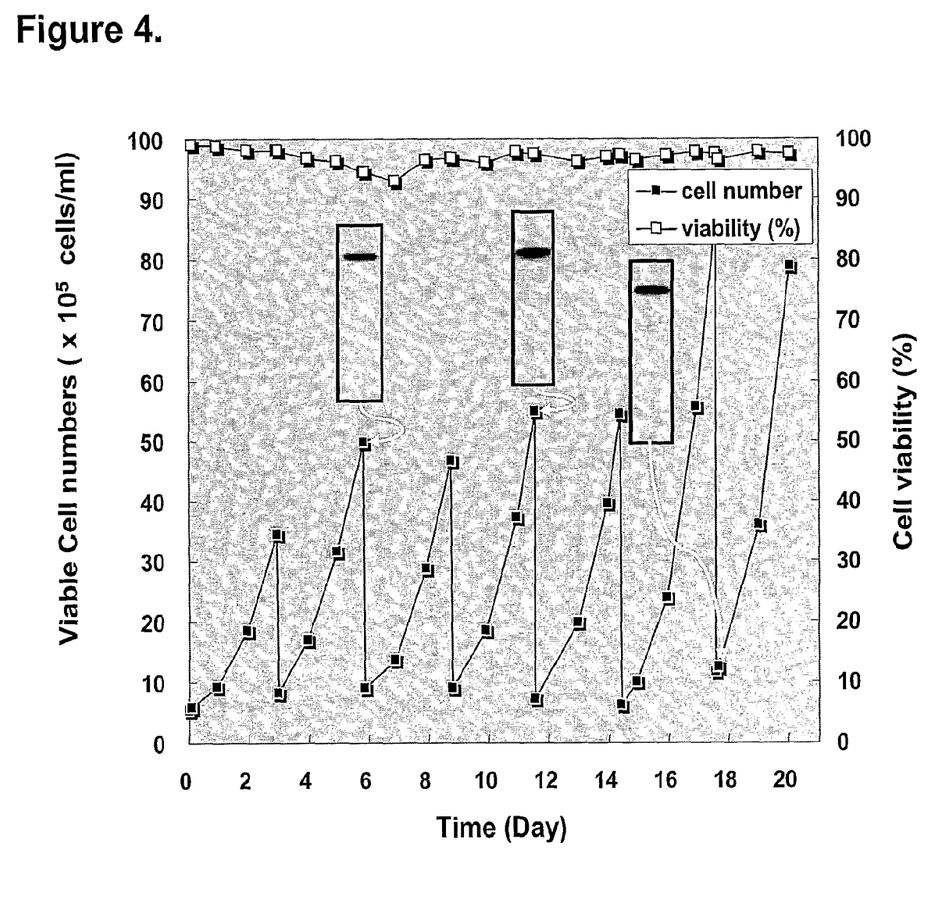
FIG. 4 shows the effect of dextran sulfate on the fragmentation of I2GdBN in perfusion culture in accordance with an embodiment of the present invention.
Figure 5:
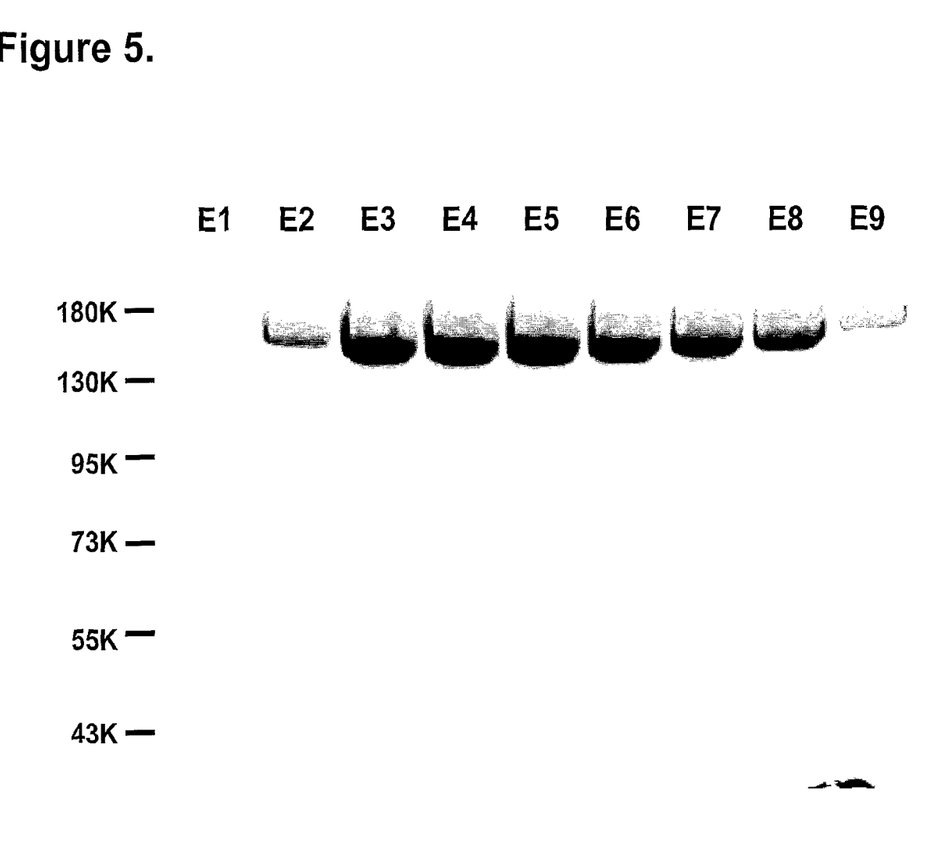
FIG. 5 shows a Coomassie Brilliant blue R250-statined SDS-PAGE gel of the elution fractions from an immunoaffinity chromatography in accordance with an embodiment of the present invention.

If dextran sulfate with a lower molecular weight can be applied to protect the cleavage, a lower molecular weight of dextran sulfate may be easily separated from factor VIII more based on its difference in size. So, to see if lower molecular weight of dextran sulfate can protect the cleavage of expressed I2GdBN during cell cultivation, 8 kDa, 10 kDa and 500 kDa dextran sulfate, which have the same content of sulfur and originated from the same source, were added to the medium at varying concentrations of 100 mg/L, 200 mg/L, 400 mg/L and 1000 mg/L. At 72 hours after addition of dextran sulfate, culture medium was harvested and analyzed by Western blotting assay. As shown in FIG. 2, although an increasing amount of dextran sulfate with low molecular weight (lane 1 to lane 8 in FIG. 2) was added into the cell culture medium, there was not observed any efficient protective effect on I2GdBN cleavage. Only 500 kDa dextran sulfate (lane 9 to lane 12) was shown to protect the fragmentation of single chain I2GdBN.

EXAMPLE 3

Only Sulfated Dextran can Protect the Cleavage

To see if a separate functional group of dextran sulfate has the inhibitory effect of cleavage, equimolar amounts of dextran (500 kDa), sodium sulfate, and dextran sulfate (500 kDa) were added in the culture medium. Cells were seeded as described in experiments. At 24 hours after seeding, several concentrations ranging from 250 mg/L to 1000 mg/L of dextran sulfate (500 kDa) and dextran (500 kDa) or several concentrations ranging from 71 g/L to 384 g/L of sodium sulfate were added to the medium. At 48 hours after addition, medium was collected from each well and analyzed by Western blot assay. As shown in FIG. 3, only 500 kDa dextran sulfate (lane 5 to lane 7) showed protective effect on cleavage of I2GdBN as depicted in FIG. 3. Neither dextran only (lane 2 to lane 4) nor sodium sulfate (lane 8 to lane 10) was shown to inhibit the protease activities of released protease(s) during CHO cultivation. Fragmentation pattern of culture medium with either dextran or sodium sulfate only was similar to that of the culture medium with no additives (control, lane 1).

EXAMPLE 4

Application of Dextran Sulfate to Suspension Culture

Dextran sulfate (500 kDa) was applied to a perfusion culture system. One vial of cell was thawed and expanded in T75 flask and further expanded in T125 flask. Cells in T125 flask were transferred into 250 ml, 1 L and 3 L spinner flasks serially and maintained as suspension culture on a magnetic stirrer plate at 37° C. in 5% of $CO^2$/air mixture with a rotation speed of 100 rpm. Exponentially growing cells in 3 L spinner flask were collected and inoculated into 7.5 L bioreactor with a working volume of 5 L. Dextran sulfate (500 kDa) was added at the concentration of 200 mg/L in the serum free medium in the bioreactor. From the fourth day after inoculation, the culture medium was collected every second day for 20 days. Cell viability was maintained above 92.7% during culture perfusion, and factor VIII fragment was detected less than 5% judged by densitometric analysis of each band in Western blot during fermentation process. Exemplary Western blots of culture media collected on day 6, day 12 and day 18 were included in FIG. 4.

EXAMPLE 5

Purification of 12GdBN from Culture Media by Immunoaffinity Chromatography

Due to the highly negative characteristic of dextran sulfate, ionic exchange chromatography cannot be applied to purify secreted factor VIII in culture media supplemented with dextran sulfate. Therefore, culture media produced in example 4 were concentrated by the tangential flow ultrafiltration and subjected to an immunoaffinity column pre-equilibrated with equilibration buffer (20 mM of Tris-HCl [pH 7.0], 400 mM NaCl, 5 mM $CaCl_2$, 3 mM EDTA). Immunoaffinity column was prepared by coupling monoclonal anti-factor VIII that recognizes A2 region of factor VIII heavy chain, to CNBr-activated sepharose resins. Factor VIII-bound immunoaffinity column was washed with 2.5 bed volume of equilibration buffer and 2.5 bed volume of washing buffer (20 mM of Tris-HCl [pH 7.0], 400 mM NaCl, 5 mM $CaCl_2$, 3 mM EDTA, 10% ethylene glycol). Elution was performed in a stepwise gradient elution with elution buffers containing ethylene glycol at the concentration ranging from 40-60%. Nine of 12 elution fractions (elution fraction number 1 to 9 corresponded to E1 to E9 in FIG. 5) were sampled and subjected to 7.5% of SDS-PAGE and stained with Coomassie brilliant blue R 250 dye. Only one-step purification of the culture medium gave more than 95% of highly pure single-chain factor VIII as illustrated in FIG. 5.

What is claimed is:

1. A method for reducing factor VIII-cleaving activities of proteases released during cell cultivation and for increasing homogeneity of recombinant factor VIII, wherein said recombinant factor VIII is produced from mammalian host cells transformed with an expression DNA vector containing cDNA coding for FVIII or FVIII derivatives in a culture medium, and said recombinant factor VIII is purified using factor VIII specific affinity molecules linked to a solid support, said method comprising:

(a) culturing said mammalian host cells in a culture medium, which is supplemented with dextran sulfate having an average molecular weight of 20 to 5,000 kDa;

(b) concentrating said culture medium containing recombinant factor VIII through ultrafiltration; and
(c) purifying said factor VIII from the concentrated culture medium by an immunological method;
wherein said recombinant factor VIII is dBN(64-53); and
wherein said factor VIII-cleaving activities of proteases released during cell cultivation are reduced and homogeneity of said recombinant factor VIII is increased.

2. The method according to claim 1, wherein the amount of said dextran sulfate in said culture medium is 10 mg/L to 2 g/L.

3. The method according to claim 1, wherein said culture medium is a medium free of an animal protein.

4. The method according to a claim 1, wherein said mammalian host cells are CHO, BHK, or COS cells.

5. The method according to claim 1, wherein said immunological method is an immunoprecipitation or an immunoaffinity chromatography.

* * * * *